(12) United States Patent
Deluis et al.

(10) Patent No.: US 6,176,839 B1
(45) Date of Patent: Jan. 23, 2001

(54) METHOD AND SYSTEM FOR TREATMENT WITH ACOUSTIC SHOCK WAVES

(75) Inventors: Michael Deluis, Munich; Reiner Reiner Schultheiss, Salem, both of (DE)

(73) Assignee: HMT High Medical Technologies AG (CH)

( * ) Notice: Under 35 U.S.C. 154(b), the term of this patent shall be extended for 0 days.

(21) Appl. No.: 09/120,547

(22) Filed: Jul. 22, 1998

(30) Foreign Application Priority Data

Aug. 4, 1997 (DE) .............................................. 197 33 838

(51) Int. Cl.$^7$ ................................................. A61B 17/225
(52) U.S. Cl. ..................................................... 601/2; 601/4
(58) Field of Search ........................... 600/439; 601/2–4; 220/581

(56) References Cited

U.S. PATENT DOCUMENTS 5,209,221 * 5/1993 Riedlinger ................................ 601/2

* cited by examiner

*Primary Examiner*—Ruth S. Smith
(74) *Attorney, Agent, or Firm*—Eugene E. Renz., PC

(57) ABSTRACT

A method and a system for the treatment of a target area within the body of a human being or animal with acoustic shock waves, consisting of the step of generating shock waves outside the body, passing the shock waves through at least some body tissue, focusing the shock waves on the target area, putting at least some of the body tissue through which the shock waves pass under a positive pressure which is greater than the surrounding air pressure and a system.

15 Claims, 4 Drawing Sheets

METHOD AND SYSTEM FOR TREATMENT WITH ACOUSTIC SHOCK WAVES

FIELD OF THE INVENTION

The present invention relates to a method for treating a target area inside the body of a human being or animal with acoustic shock waves and to a system for implementing this method.

BACKGROUND OF THE INVENTION

Acoustic shock waves are used in medicine for various indications. It is known that tumors and bodily secretions, such as gallstones, can be destroyed by acoustic shock waves. It is also known that the formation of new bone tissue can be induced and promoted by shock waves. Finally, shock waves are also used for pain therapy.

In all these applications, the shock waves act on a target area inside the body. For this purpose it is necessary for the shock waves, which are generated outside the body, to pass through body tissue to arrive at the target area and be focussed on this area. Depending on the type of treatment, it is intended and desired that the shock waves act with a greater or lesser degree of effectiveness in the target area. The body tissue through which the shock waves pass on their way to the target area, however, should interact as little as possible with the shock waves, because such interaction can lead to undesirable damage to this body tissue.

So far, damage to the body tissue located outside the target area has been minimized essentially by focussing the shock waves. The shock waves passing through the body tissue outside the target area thus have a relatively low energy density, whereas the density of the shock waves in the target areas increased by focussing.

SUMMARY OF THE INVENTION

The invention is based on the task of making available a method and device by means of which, in the treatment of target areas with shockwaves located inside the body, the damage to body tissue outside the target area can be reduced.

The invention is based on the realization that the effects of acoustic shock waves are reduced when the substance on which the shock waves are acting is put under a positive pressure. It has also been discovered that even a relatively small amount of positive pressure significantly reduces the effects of shock waves on the soft tissues of human beings and animals, whereas the effectiveness of the shock waves on bodily concretions, bone, and cartilage is only very slightly reduced by such small amounts of positive pressure and begins to decline significantly only at relatively high positive pressures.

The invention takes advantage of this realization by providing that, during the treatment with acoustic shock waves, a positive pressure is exerted on the tissue through which the shock waves must pass on their way to the target area. As a result, the effect of the shock waves on this body tissue is reduced, and damage to the body tissue by the shock waves passing through can be minimized.

Because the target area in which the shock waves are to exert their effects is usually surrounded by body tissue, it is usually impossible to exert positive pressure on the tissue located outside the target area without at the same time exerting some positive pressure on the target area as well. Because the positive pressure therefore usually acts both on the body tissue penetrated by the shock waves and on the target area, the range of positive pressures used is preferably selected in such a way that the interaction between the shock waves and the soft tissue is decreased to a very low value, whereas the interaction between the shock waves and the tissue of the target area is only slightly reduced. This range of positive pressures is to be found at approximately 30 kPa to 1 MPa above the surrounding air pressure. The best results are obtained in a range of positive pressures extending from approximately 100 to 400 kPa. In this pressure range, there is minimal interaction between the shock waves and the soft tissue, but the interaction between the shock waves and the concretions, bone, or cartilage in the target area is still high and does not begin to decrease significantly until the pressure is increased beyond this range.

In the treatment of soft tissue with shock waves, e.g., in the treatment of soft tissue pain in orthopedic medicine, positive pressure can also have the effect of decreasing the occurrence of damage in the target area which exceeds the desired positive effect of the shock waves.

BRIEF DESCRIPTION OF THE DRAWINGS

These and other objects of the present invention and various features and details of the operation and construction thereof are hereinafter more fully set forth with reference to the accompanying drawings, wherein.

The effectiveness of the method according to the invention is documented on the basis of the test results presented in FIGS. 1–3.

DESCRIPTION OF THE METHOD AND SYSTEM

Several different methods and systems for putting the body tissue under positive pressure are provided.

It is possible to put the body tissue under a constant, static positive pressure. For this purpose, the body area to be treated with the acoustic shock waves can be enclosed and sealed inside a pressurized vessel (Vp), in which a pressure medium, preferably air, is contained under elevated pressure. Such pressurized vessels (Vp) are easily designed when the treatment is conducted on the patient's extremities.

Figure 5:
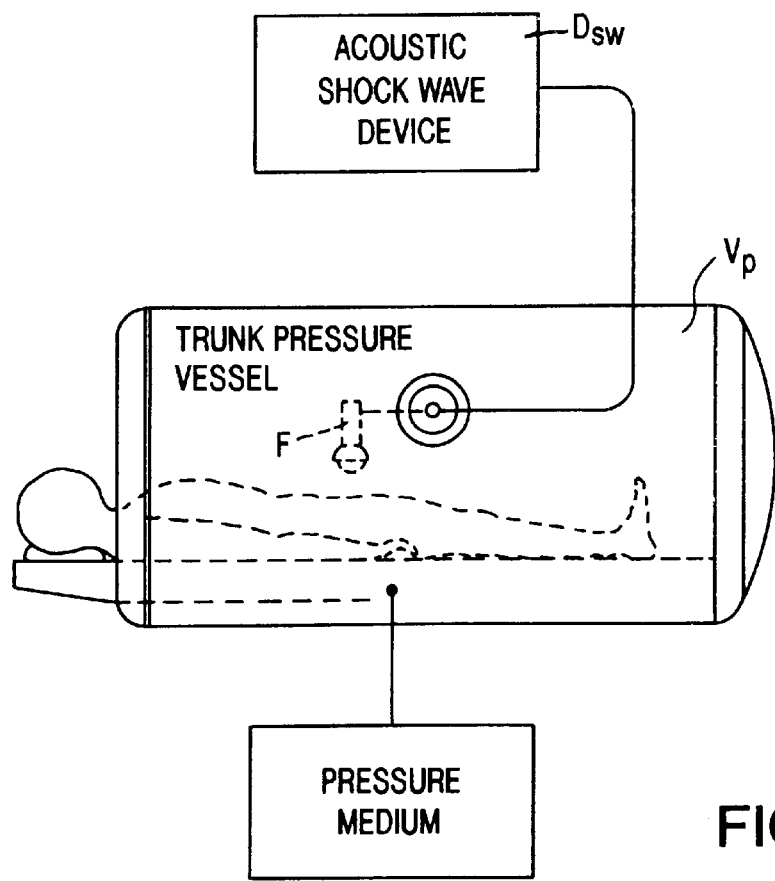
FIG. 5 is another schematic illustration showing a method for subjecting the trunk of the body to static positive pressure while undergoing treatment with acoustic shock waves in this instance an iron lung like device is used.
Figure 6:
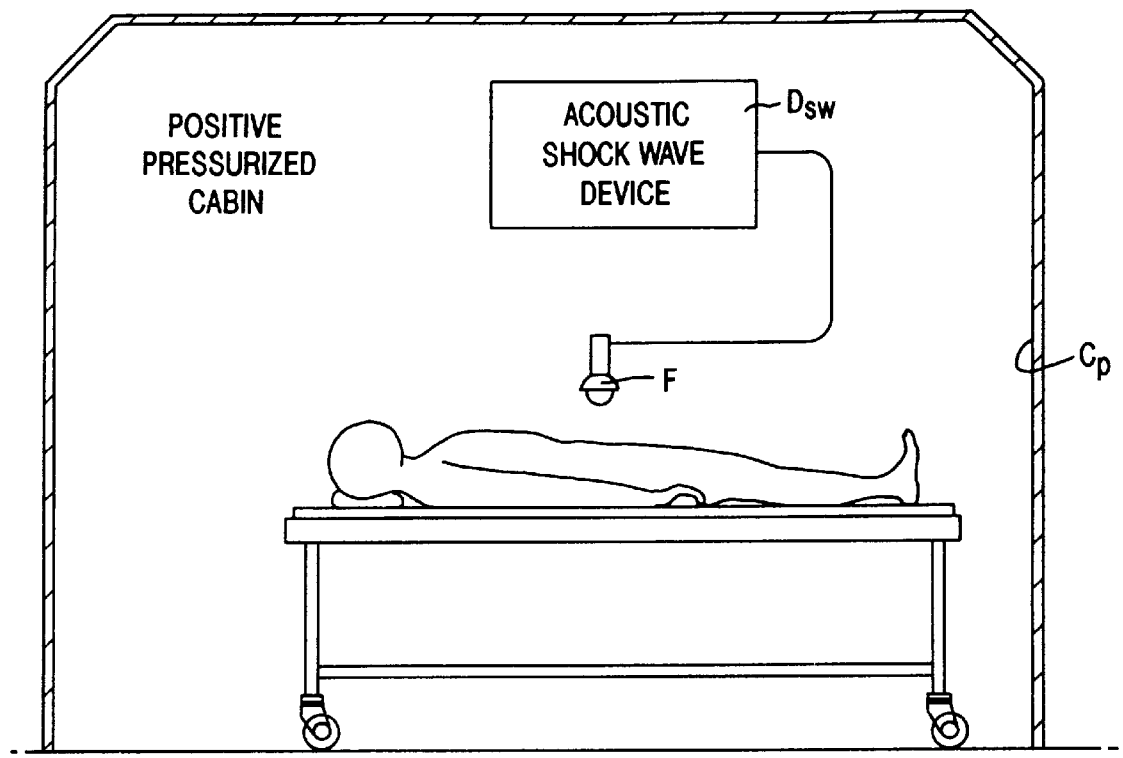
FIG. 6 is a schematic illustration showing the entire body subjected to static positive pressure while undergoing treatment with acoustic shock waves by placing the body within a pressurized cabin (Cp) or clean room.

The bodily member can be introduced into the pressure vessel through a sealable opening. If a treatment is to be conducted on the trunk of the patient, a pressurized vessel (Vp) can be used which encloses the trunk (see FIG. 5). Pressurized vessels (Vp) of this type are known under the name "iron lung",for example. If it is difficult to isolate the areas of the body to be treated so that positive pressure can be exerted on them, it is also possible to enclose the entire patient inside a pressurized cabin (Cp) (see FIG. 6). Because only a relatively slight positive pressure is used, the entire room in which the treatment takes place can also be put under positive pressure as is standard practice in, for example, "clean room" technology.

Figure 7:
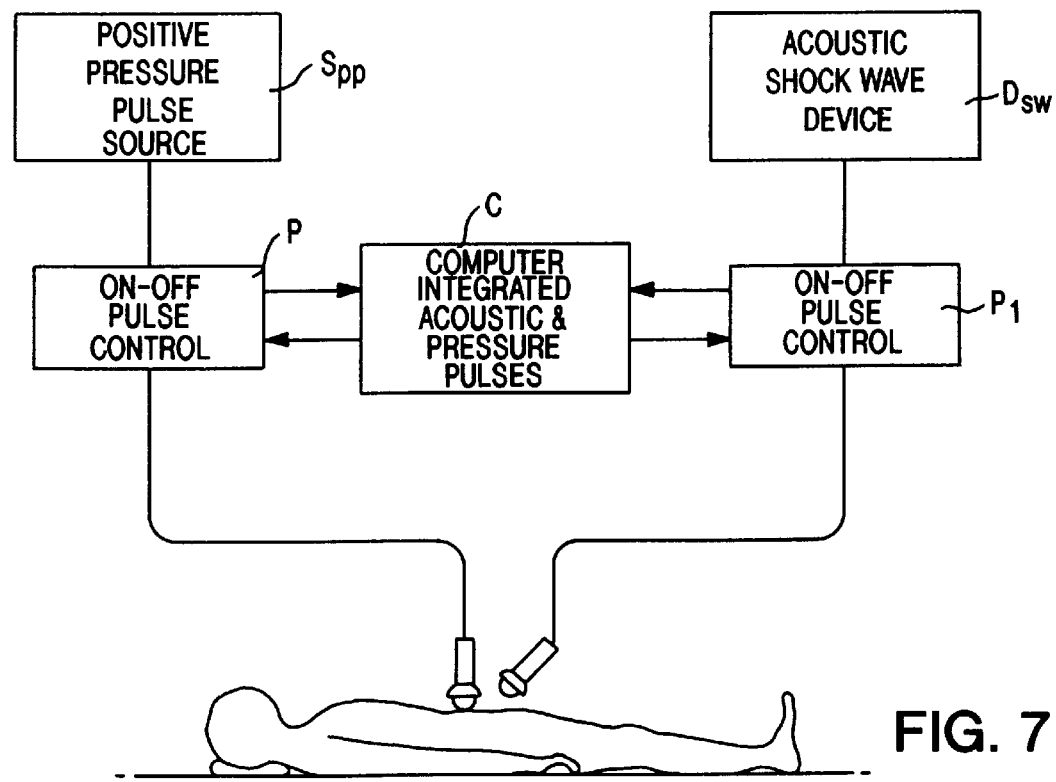
FIG. 7 is still another schematic illustration showing a means for putting the body tissue under positive pressure by means of pressure pulses of limited duration such as low frequency ultrasonic waves while undergoing treatment with acoustic shock waves.

Instead of a static positive pressure applied from the outside, it is also possible to put the body tissue under positive pressure by means of pressure pulses of limited duration as illustrated schematically in FIG. 7. This system includes a positive pressure pulse source (Spp), an on-off pulse control (P) an acoustic shock wave device (Dsw) including an associated on-off pulse control (P1) and a computer (C) to integrate and control the acoustic and pressure pulses. The duration of the positive pressure pulses must be greater than the duration of the shock wave pulses to ensure that the positive pressure remains in effect on the tissue while the shock waves are passing through. Positive pressure pulses of this type can be produced by mechanical or electromagnetic pressure-generating means. For example, low-frequency ultrasonic waves can be used, the period of which is significantly longer than the duration of the shock wave pulse. In this case, the shockwave pulses will be synchronized with the ultrasonic waves in such a way that the shock wave pulses coincide with the positive pressure half-waves of the ultrasonic waves.

The shock waves were generated by an electrohydraulic Donier XL1 lithotriptor with a capacitance of 80 nF and a shock wave pulse frequency of 1 Hz.

To determine quantitatively the damaging effect of the shock waves, two measurements were made. First, red blood cells were exposed to the shockwaves, and the amount of hemoglobin released from them by the shock waves was determined. Second, leukemia cells were exposed to the shock waves, and the permeability of the cell membrane to propidium iodine was measured. The damage makes the cell membrane permeable to propidium iodide. The smaller the number of propidium iodide-permeable cells, the less severe the damage.

To determine the effectiveness of the shock waves on the target area to be treated, gallstones were exposed to the shock waves. The effectiveness of the shock waves was measured by determining the number of gallstone fragments with a diameter of less than 2 mm. A decrease in the number of small fragments means a decrease in the effectiveness of the shock waves.

Figure 1:
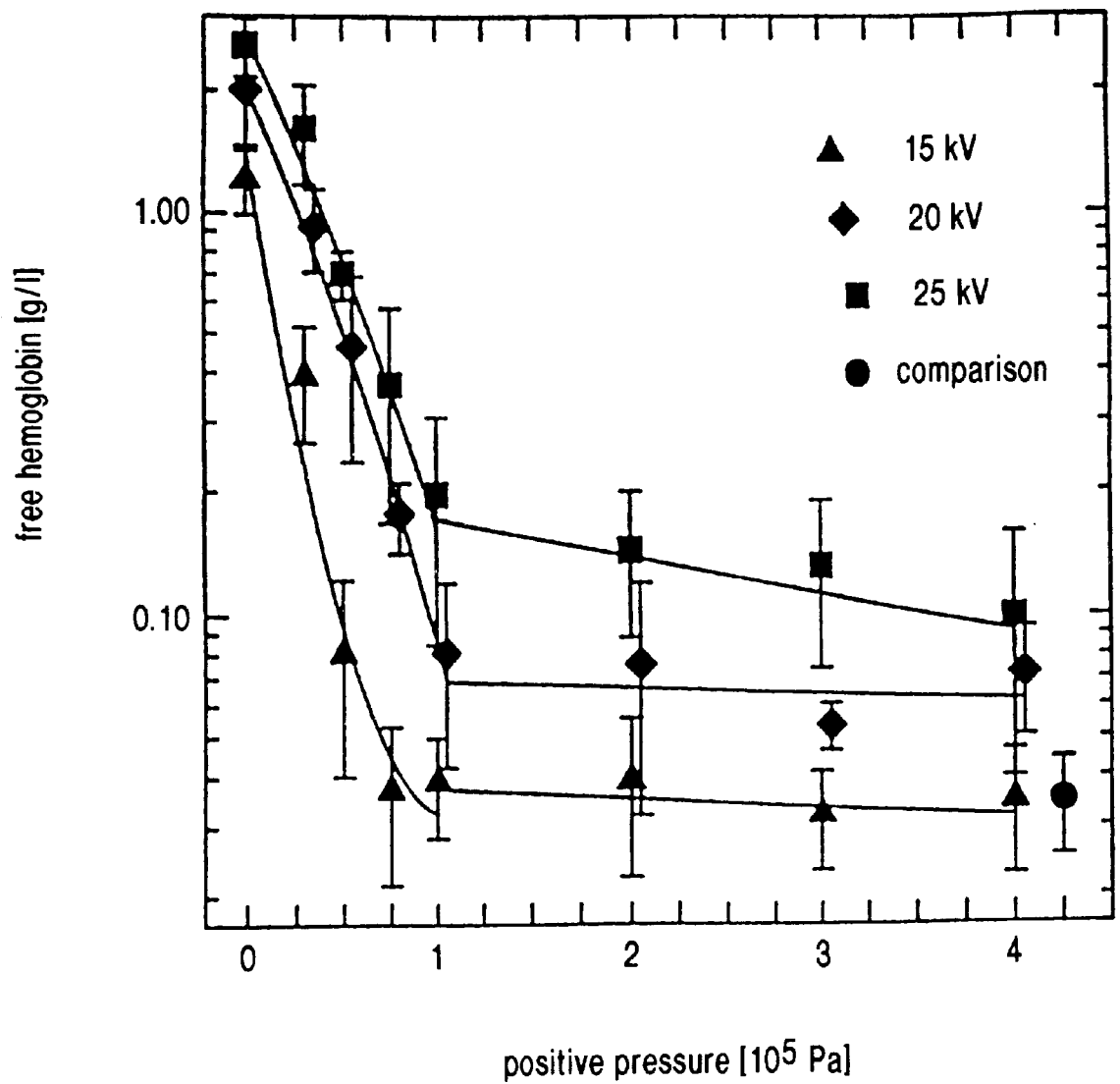
FIG. 1 is a chart showing the amount of free hemoglobin as a function of the positive pressure exerted on the cell substances.

FIG. 1 shows the amount of free hemoglobin as a function of the positive pressure exerted on the cell substance. The measurement values are plotted at shock wave discharges of 15 kV, 20 kV, and 25 kV. It can be seen that even at a positive pressure of only 30 kPa, there is already a significant decrease in the amount of free hemoglobin and thus in the amount of cell damage. This steep decrease continues all the way to a positive pressure of about 100 kPa. At approximately 100 kPa, only a small amount of free hemoglobin can be detected. An additional increase in the positive pressure up to about 400 kPa leads to no significant further reduction in the amount of free hemoglobin. The comparison value shown on the right in the graph shows the baseline value for free hemoglobin, that is, the value which is found in the absence of any action by shock waves.

Figure 2:
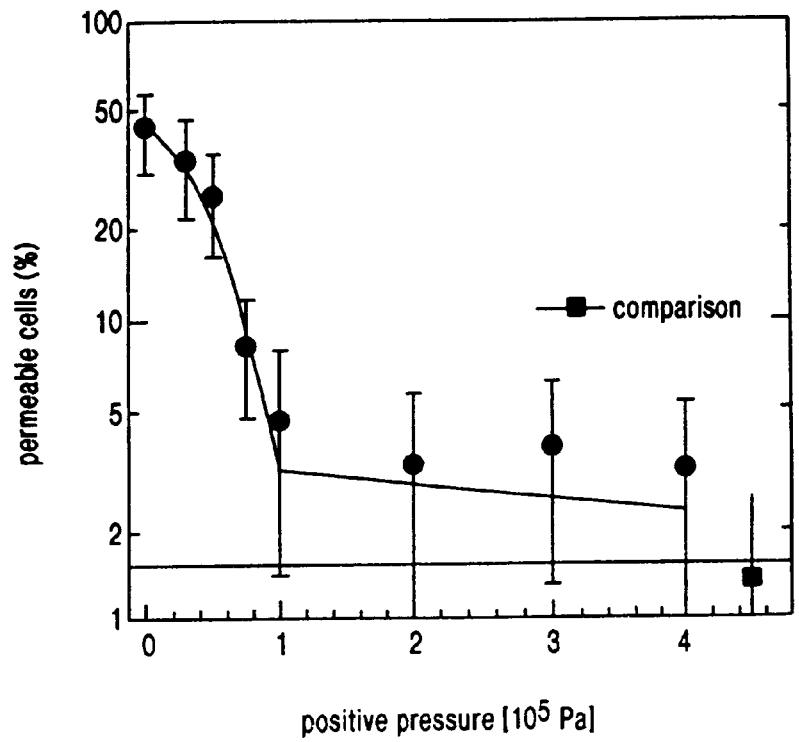
FIG. 2 is a chart showing the number or propidium iodide-permeable cells as a function of positive pressure.

FIG. 2 shows the number or propidium iodide-permeable cells as a function of the positive pressure. Here, too, the percentage of permeable, that is, damaged, cells decreases quickly up to a positive pressure of 100 kPa and then no longer changes significantly in the range from 100 kPa to 400 kPa.

Figure 3:
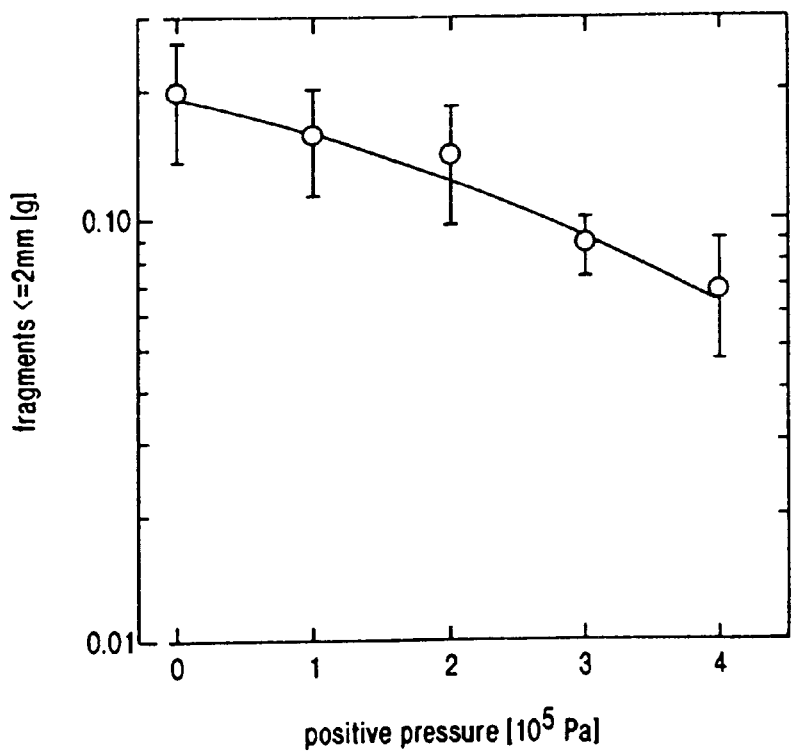
FIG. 3 is a chart showing the breakup of gallstone into fragments smaller than 2 mm as a function of the positive pressure.
Figure 4:
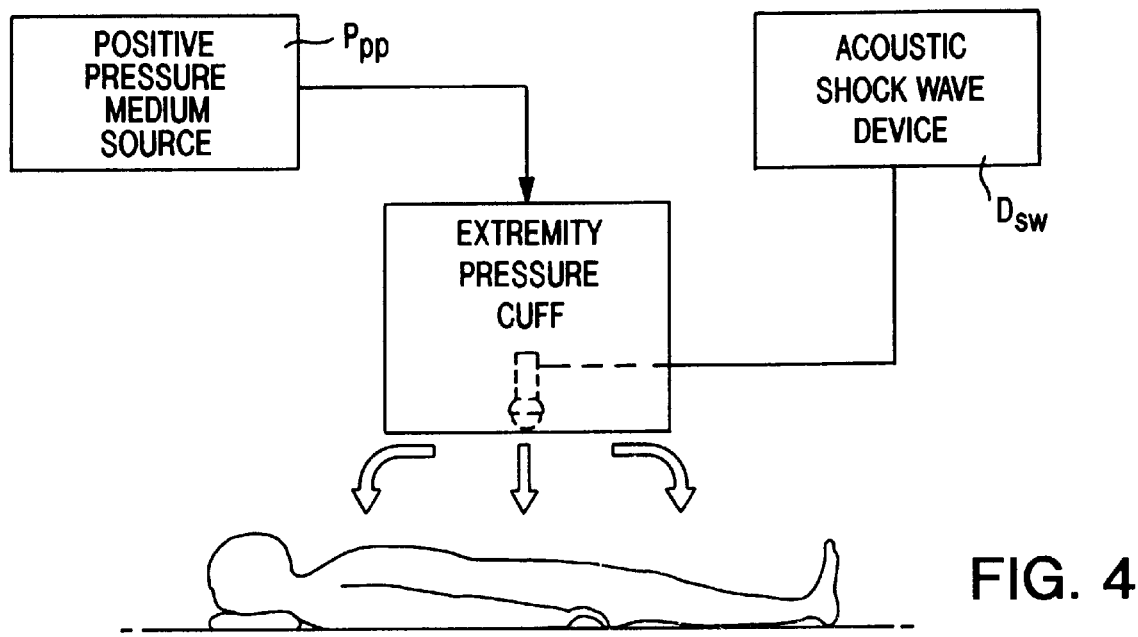
FIG. 4 is a schematic illustration showing a method for placing selected body tissue under constant static positive pressure involved in the area to be treated with acoustic shock waves in this illustration an extremity cuff is used.

FIG. 3 shows the breakup of gallstones into fragments smaller than 2 mm as a function of the positive pressure. As the positive pressure is increased from 0 to 400 kPa, there is at first only a barely detectable reduction of small fragments, which is then followed by a slow decrease in the number of these small fragments. That is, the effectiveness of the shock waves in terms of the destruction of the gallstones decreases only slightly.

The studies show that the damage to the tissue through which the shockwaves pass decreases significantly when a positive pressure is exerted on the tissue. The amount of damage decreases rapidly up to a positive pressure of 100 kPa. Above about 100 kPa, the amount of damage is minimal and can art barely be measured. The effectiveness of the shock waves on more solid substances such as body concretions, bone, and cartilage, however, decreases slowly as the positive pressure increases. Even at a positive pressure of more than 100 kPa, the shock waves are still nearly as effective as they are in the absence of pressure.

It can thus be concluded that, for the method according to the invention, it is especially advantageous for the body area of the patient to be treated to be subjected to a positive pressure ranging from approximately 100 kPa to 400 kPa. In this positive pressure range, the shock waves cause only minimal damage to the body tissue through which they pass, whereas their effectiveness in the target area is only slightly reduced.

Even though a particular embodiment of the invention has been illustrated and described herein, it is not intended to limit the invention and changes and modifications may be made therein within the scope of the following claims.

What is claimed is:

1. A system for the treating a target area within a human or animal body with acoustic shock waves, comprising:
   a shock wave generating source for generating shock waves having a positive and a negative phase;
   means for focusing said shock waves generated by said shock wave source;
   means for applying positive pressure pulses to said human or animal body independent of said shock wave generating source; and
   means for synchronizing said shock wave pulses and said positive pressure pulses such that said positive pressure pulses reduce or cancel the amplitude of the negative phase of said shock wave pulses.

2. Method for the treatment of a target area within the body of a human being or animal with acoustic shock waves, comprising the steps of generating shock waves outside the body, passing the shock waves through at least some body tissue, focusing the shock waves on the target area, putting at least some of the body tissue through which the shock waves pass under a positive pressure which is greater than the surrounding air pressure wherein a constant, static positive pressure is exerted throughout the treatment.

3. A method according to claim 2 characterized in that the positive pressure is approximately 30 kPa to 1 MPa greater than the surrounding air pressure.

4. A method according to claim 3 characterized in that the positive pressure is approximately 100–400 kPa greater than the surrounding air pressure.

5. Method for the treatment of a target area within the body of a human being or animal with acoustic shock waves, comprising steps of generating shock waves having a pulse duration outside the body, passing the shock waves through at least some body tissue, focusing the shock waves on the target area, putting at least some of the body tissue through which the shock waves pass under a positive pressure which is greater than the surrounding air pressure wherein the positive pressure is exerted in the form of pulses of limited duration, the pulse duration being longer than the pulse duration of the shock waves, and in that the shock waves act while said pulse of limited duration exerting the positive pressure is in effect.

6. A method according to claim 5 in that the positive pressure is approximately 30 kPa to 1 MPa greater than the surrounding air pressure.

7. Method for the treatment of a target area within the body of a human being or animal with acoustic shock waves, comprising the steps of generating shock waves outside the body, passing the shock waves through at least some body tissue, focusing the shock waves on the target area, putting at least some of the body tissue through which the shock waves pass under a positive pressure which is greater than the surrounding air pressure wherein the positive pressure is generated by a vessel enclosing at least part of the body, in which vessel a pressure medium is put under static positive pressure.

8. A method according to claim 7 in that the positive pressure is approximately 30 kPa to 1 MPa greater than the surrounding air pressure.

9. Method for the treatment of a target area within the body of a human being or animal with acoustic shock waves, comprising the steps of generating shock waves having a pulse duration outside the body, passing the shock waves through at least some body tissue, focusing the shock waves on the target area, putting at least some of the body tissue through which the shock waves pass under a positive pressure which is greater than the surrounding air pressure wherein positive pressure is generated by ultrasonic waves, the positive pressure half-period of which is longer than the pulse duration of the shock waves, and in that the shock waves act during the positive pressure half-period of the ultrasonic waves.

10. A method according to claim 9 in that the positive pressure is approximately 30 kPa to 1 MPa greater than the surrounding air pressure.

11. A system for treating a target area within the body of a human being or animal with acoustic shock waves, comprising at least one shock wave source (Dsw) means for focusing (F) the shock waves generated by the shockwave source, and a mechanism for generating a positive pressure in at least part of the area of the body tissue through which the shock waves pass.

12. A system according to claim 11, characterized in that the pressure medium is air, and wherein the mechanism comprises a pressurized vessel (Vp) connected to a source of compressed air which is adapted to enclose and seal off at least one body area to be treated.

13. A system according to claim 11, wherein the mechanism comprises a pressurized cabin (Cp) or a room which is adapted to enclose the entire patient.

14. A system according to claim 11, wherein the mechanism comprises a positive pressure pulse source (Spp) for generating positive pressure pulses, the pulse duration of which is longer than the pulse duration of the shock waves.

15. A system according to claim 14, wherein the positive pressure pulse source generates ultrasonic waves, the positive pressure half-period of which is longer than the pulse duration of the shockwaves.

\* \* \* \* \*

UNITED STATES PATENT AND TRADEMARK OFFICE
CERTIFICATE OF CORRECTION

PATENT NO. : 6,176,839
DATED : January 23, 2001
INVENTOR(S) : DELIUS

It is certified that error appears in the above-identified patent and that said Letters Patent is hereby corrected as shown below:

On title page, item

(75) Assignee:-Michael Delius, Munich; Reiner Schultheiss, Salem, both of (DE)--

Signed and Sealed this

Fifth Day of June, 2001

Attest:

NICHOLAS P. GODICI

*Attesting Officer*

*Acting Director of the United States Patent and Trademark Office*